US012758563B2

(12) United States Patent
Mason

(10) Patent No.: US 12,758,563 B2
(45) Date of Patent: Oct. 13, 2026

(54) PHARMACEUTICAL COMPOUNDS AND METHODS OF USE

(71) Applicant: DERMCARE-VET PTY LTD, Slacks Creek (AU)

(72) Inventor: Kenneth Vincent Mason, Slacks Creek (AU)

(73) Assignee: DERMCARE-VET PTY LTD, Slacks Creek (AU)

( * ) Notice: Subject to any disclaimer, the term of this patent is extended or adjusted under 35 U.S.C. 154(b) by 1056 days.

(21) Appl. No.: 17/762,519

(22) PCT Filed: Sep. 23, 2020

(86) PCT No.: PCT/AU2020/051003
§ 371 (c)(1),
(2) Date: Mar. 22, 2022

(87) PCT Pub. No.: WO2021/056056
PCT Pub. Date: Apr. 1, 2021

(65) Prior Publication Data

US 2022/0354871 A1 Nov. 10, 2022

(30) Foreign Application Priority Data

Sep. 23, 2019 (AU) ................................ 2019903522

(51) Int. Cl.
*A61K 31/58* (2006.01)
*A61K 9/00* (2006.01)
*A61K 31/216* (2006.01)

(52) U.S. Cl.
CPC ............ *A61K 31/58* (2013.01); *A61K 9/0014* (2013.01); *A61K 31/216* (2013.01)

(58) Field of Classification Search
CPC ..... A61K 31/58; A61K 9/0014; A61K 31/216
See application file for complete search history.

(56) References Cited

U.S. PATENT DOCUMENTS

| | | | | |
|---|---|---|---|---|
| 4,607,050 A * | 8/1986 | Kieran .................. | A01N 25/06 514/531 |
| 2016/0262397 A1 | 9/2016 | Mastroianni | |
| 2018/0035675 A1 | 2/2018 | Joshi et al. | |

FOREIGN PATENT DOCUMENTS

| | | |
|---|---|---|
| CN | 105560252 | 5/2016 |
| CN | 109464390 | 3/2019 |
| JP | 2014521634 A | 8/2014 |
| WO | 03086348 A1 | 10/2003 |

(Continued)

OTHER PUBLICATIONS

Ahlstrom et al. (J. Vet Pharmacol. Therap. 2010; 33: 573-582). (Year: 2010).*

(Continued)

*Primary Examiner* — Clinton A Brooks
*Assistant Examiner* — Jerica Katlynn Wilson
(74) *Attorney, Agent, or Firm* — Barnes & Thornburg LLP

(57) ABSTRACT

The present invention relates to pharmaceutical compositions for topical use comprising a corticosteroid and an insecticide selected from pyrethrin or a synthetic pyrethroid insecticide. Methods for their use in treating allergic dermatitis, particularly insect bite hypersensitivity, in animals using the compositions of the invention are also described.

20 Claims, 3 Drawing Sheets

(56) References Cited

FOREIGN PATENT DOCUMENTS

WO 2013014597 A1 1/2013

OTHER PUBLICATIONS

Jachowicz (Iscc Monograph. 2004: 1-295). (Year: 2004).*
Ahlstrom et al. (The Veterinary Journal.2013; 196: 456-460) (Year: 2013).*
Ihrke et al. (World Small Animal Veterinary Association World Congress Proceedings. How I Treat Flea Allergy Dermatitis in 2008. 2008) (Year: 2008).*
Schalau et al. (Dow Corning Corporation. Recent Developments on Silicones in Topical and Transdermal Drug Delivery. 2017). (Year: 2017).*
PCT Search Report and Written Opinion prepared for PCT Application No. PCT/AU2020/051003, completed Nov. 23, 2020.
Schalau, G., et al. "Silicone Excipients in Pharmaceutical Drug Delivery Applications," 2015, Silicone Excipients in Pharmaceutical Drug Delivery Applications. In: Narang A., Boddu S. (eds) Excipient Applications in Formulation Design and Drug Delivery. Springer, Cham. Book reference; available on request.
Ahlstrom, LA et al, "The effects of formulation on the penetration and retention of budesonide in canine skin in vitro", The Veterinary Journal, 196 (2013) 456-460.
Dawn Merton Boothe (2012), Glucocorticoids and Mineralocorticoids. In Dawn Merton Boothe (2nd ed.). Small Animal Clinical Pharmacology and Therapeutics (2nd ed., pp. 1131 and 1137). Elsevier Saunders.
Basic and Clinical Nasal Science, Zhen Dong (Ed.), People's Military Medical Publishing House, 1st edition of Jan. 2006, Glucocorticoids, pp. 279-281.
Olivry, Thierry et al., Evidence-based veterinary dermatology: a systematic review of the pharmacotherapy of canine atopic dermatitis, Veterinary Dermatology, Jul. 2003; 14(3):121-146.
Schaffartzik A., et al., "Equine insect bite hypersensitivity: What do we know?", Veterinary Immunology and Immunopathology, vol. 147(3), 2012, pp. 113-126.
Isabella Pali-Scholl, et al, "EAACI position paper: Comparing insect hypersensitivity induced by bite, sting, inhalation or Ingestion in human beings and animals", Allergy, vol. 74(5), 2019, pp. 874-887.

* cited by examiner

PHARMACEUTICAL COMPOUNDS AND METHODS OF USE

CROSS-REFERENCE TO RELATED APPLICATIONS

This application is a national stage entry under 35 U.S.C. § 371(b) of PCT International Application No. PCT/AU2020/051003, filed Sep. 23, 2020, which claims priority to Australian Provisional Application No. 2019903522 entitled "Pharmaceutical Compositions and Methods of Use" filed 23 Sep. 2019, the contents of both of which are incorporated herein by reference in their entirety.

This application claims priority to Australian Provisional Application No. 2019903522 entitled "Pharmaceutical Compositions and Methods of Use" filed 23 Sep. 2019, the contents of which are incorporated herein by reference in their entirety.

FIELD OF THE INVENTION

The present invention relates to pharmaceutical compositions for topical use comprising a corticosteroid and an insecticide selected from pyrethrin or a synthetic pyrethroid insecticide. Methods for their use in treating lesions and pruritus associated with allergic dermatitis, particularly insect bite hypersensitivity, in animals using the compositions of the invention are also described.

BACKGROUND OF THE INVENTION

Allergic dermatitis due to insect bites is a common condition found in animals. It occurs in all parts of the world where the animal and the respective parasite co-exist and is particularly prevalent in warmer climates. Insect bite allergic dermatitis can affect domestic animals such as sheep, cattle, pigs, horses and dogs. It is particularly prevalent in horses and dogs, and is by far the most common cause of skin disease in domestic horses and dogs.

An allergy is the hypersensitivity or altered state of the immune system that results in self-harm. Within groups of animals, only a few may be affected. There are four different types of immune reactions to an allergen. The most common type, and the one predominantly implicated in the clinical syndromes of insect bite hypersensitivity, is a Type I IgE mediated immune reaction, although type III and type IV cell mediated immunopathogeneses may also occur.

In a Type I immunopathogeneses, an allergen specific IgE binds with an antigen on a mast cell triggering degranulation and the subsequent release of histamine, serotonin, eotaxin and other cytokines. This leads to inflammation and the attraction of other inflammatory cells. For insect bite hypersensitivity, the allergens are primarily salivary antigens, with 11 salivary gland proteins of *Culicoides* spp. (midge) identified as allergens for Insect Bite Hypersensitivity (IBH) in horses (Schaffartzik et al., Veterinary Immunology and Immunopathology 147 (2012) 113-126), and numerous *Ctenocephalides felis* (cat flea) saliva proteins identified as allergens in dogs (Lee et al., Veterinary Immunology and Immunopathology 69 (1999) 229-237).

The degree of stimulation of IgE responses is dependent on the characteristics of the antigen and genetic factors of the individual affected. The insect model demonstrates both the protective and potentially destructive nature of immune system responses. The irritation of an insect bite may cause the host to respond and dislodge or kill the insect, and in the normal situation, the immune response may change leading to anergy, i.e. diminished reactivity. Alternatively, if the individual has a genetic predisposition, hypersensitivity develops and leads to persistent inflammation, which is enhanced and perpetuated by self-trauma from rubbing, chewing and scratching. Additionally, the release of histamine and other inflammatory factors, such as eicosanoids, results in an increase of blood flow and permeability of blood vessels at the site of the reaction, leading to an itch response and further skin damage via self-trauma. This cycle of itch, scratch, skin damage, and further itch, results in ongoing tissue damage and animal suffering.

This abnormal and long-lasting hypersensitivity is thought to have a genetic basis in the horse. For example, a study of Warmblood horses in the Czech Republic demonstrated that the affliction rate in the offspring of particular stallions was significantly different, ranging from 10% to 75% (Raskova et al., J. Equine Vet. Sci. 2013; 33(6):427-432), which supports the genetic predilection model. Conversely, a hereditary link has not been established, with no breed predilection identified (Miller et al. *Muller & Kirk's Small Animal Dermatology,* 7$^{th}$ ed. St. Louis, MO: Elsevier/Mosby, 2013; 4072013)

Horses are commonly afflicted by IBH to *Culicoides* spp. (biting midge). The disease is known colloquially as Queensland Itch in Australia, and Sweet Itch in the Northern Hemisphere. While *Culicoides* spp. is the most commonly implicated parasite; *Tabanus* and *Chrysops* spp. (horse flies), *Stomoxys* spp. (stable flies), *Simulium* spp. (black flies) and *Musca* spp. (house flies), as well as bees and wasps, can all cause lesions and hypersensitivity reactions in a horse's skin.

In dogs, the most common form of allergic dermatitis due to insects is Flea Allergy Dermatitis (FAD). *Ctenocephalides felis* (the "cat flea") is the main parasite involved, although *C. canis* can also be present. The term "summer itch" or "summer eczema/dermatitis" is also used colloquially for the horse and dog disease as both are summer seasonal.

The clinical signs differ between the animal species, however there are similarities in their dorsal distribution and intense pruritus. In horses, *Culicoides* spp. feed on the dorsal surface, predominantly along the mane and tail area and around the face and ears. Even in animals who do not have hypersensitivity, the bite of the *Culicoides* midge can be particularly painful, due to the chewing mouth parts.

In dogs, the clinical signs associated with FAD include a pruritic papular dermatitis on the rump, dorsal thorax, flanks, tanks and perineal area. Generalised distribution can occur in severe cases. Some dogs can develop severe acute lesions such as acral lick granuloma or pyotraumatic dermatitis on the rump or side of the face.

A horse or dog whose irritation progresses to the hypersensitivity state will have signs that progress from thinning of the hair or coat and papules and wheals to alopecia, crusting, excoriations, hypopigmentation and lichenification. When the skin becomes secondarily infected, the pruritus is often worsened. Staphylococcal isolates are commonly involved in these secondary infections.

Both IBH and FAD are known to cause significant suffering and distress to affected animals worldwide. Many treatments have been developed for the disease, with varying degrees of success and in some cases, deleterious results. Theoretically, the elimination of all biting insects (i.e. environmental control) to which the animal is allergic will resolve the dermatitis but in most circumstances, this can be difficult or impossible to achieve. Therefore, treatment should involve both minimising the insect bite and management of the pruritus resulting from the allergic reaction. To date, there is no single treatment that addresses both of these requirements, nor a formulation with a practical and reasonable administration interval. There are several drawbacks of current management and treatment modalities.

Environmental control of *Culicoides* species is difficult. The lifecycle is poorly understood, making environmental control challenging. During summer the development from egg to adult takes a couple weeks. Similar to the flea, some larvae and pupae overwinter in protected breeding places and continue development in warmer weather. The midges breed in moist conditions in a variety of habitats, particularly damp, muddy areas and in faecal and plant matter. The adult midges usually live for about 20 days and depending on ambient conditions they can live for more than 90 days. The adults fly and copulate in swarms. Like the flea, the female midges require blood meals for the maturation of their eggs. Between 100 and 200 eggs are usually laid in areas with a specific humidity and abundant organic material. Development from egg to adult usually takes about 15 days but can be up to up to seven months during the overwintering period. Modification of these areas by removing organic matter and draining muddy areas, form an important part of the control strategy for *Culicoides* breeding, however, it is still difficult to achieve complete control.

Environmental control of the flea is easier, as all breeding stages occur within the house and yard. Flea bombing and vacuuming of indoor areas, as well as treating all household animals, can provide good results.

Prevention of exposure to the biting insects is a cornerstone of current treatment protocols. For example, stabling horses at dawn and dusk and the use of fans at these times will reduce the number of *Culicoides* midges gaining access to the animal. If fans cannot be used, then mosquito netting over windows and around doors of enclosed stable areas may be helpful. In the summer months, stabling would typically be required between about 4 pm and 8 am. In warmer climates, such as sub-tropical to tropical Australia, enclosed stabling is not as readily available as it may be in more temperate climates like Europe, where horses may be stabled for much of their time. Many Australian horses are routinely kept on pasture all year round, with only shade trees and other open structures for shelter. Use of rugs ("rugging") is often used to prevent exposure to the midges instead, however rugs are inappropriate in hot summer conditions. In addition, the damage caused to the rugs from horses rubbing against fences and trees, necessitates frequent and costly repair and replacement.

It is often impractical or impossible to completely eliminate the insect from the environment or provide physical protection from either fleas or midges. Chemical repellents can be used in an attempt to prevent the insect from biting. Natural pyrethrin insect repellents are extracted from the flowers of certain chrysanthemum species, notably *Chrysanthemum cinerariifolium.*

Synthetic pyrethroid based insect control products are generally used for their insect repellent activity in both dogs and horses. These synthetic pyrethroids are more potent, have lower odour, last longer and can be used in lower concentrations than natural pyrethrins (see, for example, chemicalWATCH Factsheet: https://www.beyondpesticides.org/assets/media/documents/mosquito/documents/SyntheticPyrethroids.pdf).

Type I pyrethroids include Allethrin, Bifenthrin, Permethrin, Phenothrin, Resmethrin, Tefluthrin, and Teramethrin. Type II Pyrethroids include Cyfluthrin, Cyhalothrin, Cypermethrin, Deltamethrin, Fenvalerate, Fenpropathrin, Flucythrinate, Flumethrin, Fluvalinate, and Tralomethrin.

A disadvantage of synthetic pyrethroids is that chemical modifications to the natural pyrethrin structure to increase stability and insect repellent efficiency often result in the increase of the irritant potential of the product. Those with a cyano group tend to be more irritant. This is particularly notable in the second generation pyrethroids, such as permethrin. To avoid irritancy the concentration of permethrin can be lowered, however this has a negative effect on efficacy. As a result of the need to reduce or avoid irritancy, often insect control products do not contain a sufficiently high concentration of permethrin to be effective as an insect repellent. Alternatively, a product containing pyrethrin, a first generation compound, is used which is approximately four times less effective than permethrin, and less stable.

Commonly available insecticide treatments for horses include daily application of 40 g/L permethrin diluted to 2% as a spray or rinse or 87 g/L permethrin for administration as a once weekly pour-on application. Piperonyl butoxide in combination with permethrin may be applied to horses or dogs as a spray or rinse twice daily to twice weekly. These treatments suffer from drawbacks such as frequent application and/or skin irritation. A once weekly pour-on application of 200 g/L fenvalerate to horses causes irritation. Twice daily application of 89 g/L citronella oil and 51 g/L N, N-diethyl-M-toluamide to dogs or horses has poor efficacy against fleas and *Culicoides* and a short duration of effect. Alternate day application of permethrin/citronella combination spray or rinse to dogs or horses has a very short duration of activity. Twice daily spray or rinse application of a benzoyl benzoate/bronopol formulation is used to treat secondary skin infection in dogs or horses. This has poor efficacy on fleas and gnats; moreover bronopol is known to be a cause allergic dermatitis.

Several products for treating dogs, but not horses, are available which can be used to ensure that if the flea does get onto the animal, it dies quickly. This reduces feeding time and therefore prevents or reduces exposure to the saliva allergen. These products include topical treatments containing permethrin, fipronil or indoxacarb. Typically these can be applied to the back of the neck of the animal and subsequently spread via epidermal lipids. These products, often referred to as "spot-on" treatments, require frequent application and prevent bathing for several days prior to, and after, application. In some cases these products may have decreasing efficacy as fleas develop resistance.

Systemic products for treating dogs are also commercially available. These are usually in the form of a monthly, or three-monthly, chewable tablet comprising active ingredients such as spinosad, afoxolaner or fluralaner. In common with the topical spot-on treatments, they do not act as a repellent and require the flea to feed on the dog to ingest the active and die. However, the kill times are relatively fast. These products have the disadvantage of being relatively expensive (Pucheu-Haston et al., Practical Parasitology: The Flea Infested Pet: Overview of Current Products. Today's Vet. Pract. 7: 90-95).

To treat the allergy component of the disease, both topical and systemic glucocorticoids are used in dogs. Typically, topical polypharmacy creams are used. These usually comprise a corticosteroid, a local anaesthetic and an antibiotic. These polypharmacy compositions have the disadvantage that they contain an antibiotic component which may not be required and can result in potentially inappropriate administration which can exacerbate development of resistance.

Corticosteroid spray products, containing for example hydrocortisone aceponate in an alcohol base, are also available. Following application of the corticosteroid spray, the carrier evaporates leaving the active ingredient on the skin. This can sting broken skin, and needs to be used judiciously to avoid distressing the animal any further.

Oral prednisolone is commonly used in dogs while flea control takes effect. Typical doses are about 1 mg/kg/day, then doses are reduced gradually. Common side effects of oral prednisolone can include panting, lethargy, increased thirst and urination, and increased appetite, all of which can cause concern to the animal and owner. Long term use of oral prednisolone can result in symptoms of hypercortisolism, such as abnormal fat metabolism, alopecia and thinning of the skin.

Systemic corticosteroids used in horses to deal with the allergic component of the disease include short courses (1-2 weeks) of oral prednisolone at a dosage of 1 mg/kg daily. Alternatively, a convenient, but potentially dangerous, long acting injectable corticosteroid may be given in combination with other methods of management of the condition until the pruritus is blocked or reduced. These long acting injectable corticosteroids, such as triamcinolone acetonide, dexamethasone and methylprednisolone acetate, typically induce increased adverse steroid side effects and ongoing suppression of the pituitary hypothalamic adrenal axis. Additionally, all systemic corticosteroids are contraindicated in pregnant mares, horses with a history of laminitis, those with Equine Cushing's Syndrome or Equine Metabolic Disease, and those with any other internal organ complication.

$H_1$-Antihistamines may be used to alleviate symptoms of insect bite allergic dermatitis, however these provide no real advantage over glucocorticoids, as they have limited efficacy in reducing pruritus. Moreover, $H_1$-antihistamines also have the potential to induce light sedation and behavioural or personality changes in the animal.

Alternative forms of therapy, such as desensitisation using immunotherapy has been attempted, however this appears to induce a poor response in both horses and dogs (Ginel, et al., Vet. Dermatol. 2014; 25:29-e 10).

Recent approaches using blocking analogies or monoclonal antibodies that inactivate inflammatory cytokines are promising for the horse and have proven efficacy in the dog for flea allergy (Michaels, et al., Vet. Dermatol. 2016; 27:478-e 129). The real value in insect bite allergy remains to be assessed. However, given the research input required, this is expected to be an expensive approach in horses as it is for the currently marketed cytokine blockers for dogs. Furthermore, long term effects of blocking this pathway of the immune system is unknown.

Popular and relatively accessible remedies such as shampooing animals with oatmeal preparations has been used to provide some relief, and the application of other "natural" or accessible remedies such as calamine lotion have all been suggested, though neither is effective as a stand-alone treatment and the benefit is minimal. The use of dietary supplementation using, for example essential fatty acid, has increased in recent years, but there is limited data available to support its effectiveness. Similarly, traditional or natural remedies such as garlic supplementation in the diet have been suggested for both the control of fleas and management of the inflammation, but there is insufficient data to support any real benefit.

It is evident that the complexity of insect bite allergic dermatitis, the prevalence of the parasites worldwide, and the resulting suffering and reduced quality of life for affected animals, together with the concern and cost to owners warrants the development of a more effective treatment that addresses one or more of the drawbacks of presently available treatments. In particular, there is a need for treatments that are more effective, easy to use, have convenient application intervals, are readily accessible or are cost-effective.

SUMMARY OF THE INVENTION

Advantageously, the inventor has discovered that compositions for topical application comprising a corticosteroid in combination with a pyrethrin insecticide or a pyrethroid insecticide find use in the treatment of insect bite allergic dermatitis, or insect bite hypersensitivity, in mammals. In preferred embodiments, the compositions additionally comprise one or more silicone excipients.

The topical formulations avoid the need for systemic corticosteroids. The compositions are thus considered safe for use as they have minimal systemic toxicity or side effects. The formulations are convenient and easy to use. Moreover, the formulations are fast acting and provide rapid relief to animals suffering allergic responses.

Accordingly, in a first aspect there is provided a pharmaceutical composition for topical application comprising, consisting of or consisting essentially of a corticosteroid; an insecticide selected from pyrethrin insecticides and pyrethroid insecticides; and a pharmaceutically acceptable carrier.

Preferably, the composition is for application to the skin and/or coat of an animal. In preferred embodiments, the composition further comprises one or more silicones.

In another aspect, there is provided a method of treating insect bite allergic dermatitis in a mammal, comprising topical administration of an effective amount of a composition comprising, consisting of or consisting essentially of a corticosteroid and an insecticide selected from pyrethrin insecticides and pyrethroid insecticides to a mammal in need thereof.

In yet another aspect, there is provided a topical composition comprising, consisting of, or consisting essentially of a corticosteroid and an insecticide selected from pyrethrin insecticides and pyrethroid insecticides for use in treatment of insect bite allergic dermatitis.

In a yet further aspect, there is provided a use of a topical composition comprising, consisting of, or consisting essentially of a corticosteroid and an insecticide selected from pyrethrin insecticides and pyrethroid insecticides in the manufacture of a medicament for treatment of insect bite allergic dermatitis.

In some embodiments, the corticosteroid is budesonide.

In some embodiments, the insecticide is permethrin.

In some embodiments, the composition comprises budesonide in an amount of about 0.2 g/L to about 1 g/L, for example approximately 0.25 g/L; and permethrin in an amount of amount of about 20 g/L to about 80 g/L, for example approximately 40 g/L.

A composition is preferably formulated in a base comprising one or more conditioning excipients, for example one or more silicones.

In some embodiments, the composition comprises one or more silicones totaling from about 25 g/L to about 150 g/L of the composition, for example about 75 g/L of the composition.

In some embodiments, the pharmaceutical composition is a conditioner, a leave-in (or leave on) conditioner, a lotion, a spray, a cream, an ointment or a pour-on formulation.

In some embodiments, the pharmaceutical formulation is adapted for application, preferably to the skin, coat or hair of the animal, by pouring or spraying. In some embodiments, the composition is formulated for application by smoothing into to the coat of the animal.

In some embodiments, the mammal is an equine or a canine.

In yet another aspect, there is provided a pharmaceutical composition formulated for topical administration comprising, consisting of, or consisting essentially of:

- a corticosteroid in an amount of about 0.025 g/L to about 1 g/L, or 0.15 g/L to about 1 g/L;
- a pyrethrin insecticide or a pyrethroid insecticide in an amount of about 0.5 g/L to about 50 g/L;
- one or more silicones in an amount of about 25 g/L to about 150 g/L;
- at least one pharmaceutically acceptable excipient; and
- a pharmaceutically acceptable aqueous carrier.

In yet another aspect, there is provided a pharmaceutical composition formulated as a leave-in (or leave on) conditioner for topical administration comprising, consisting of, or consisting essentially of:

- budesonide in an amount of about 0.25 g/L;
- permethrin in an amount of about 40 g/L;
- one or more silicones in a combined amount of about 75 g/L;
- thickening agents in an amount of about 30 g/L;
- one or more pharmaceutically acceptable excipients selected from solubilizing agents, chelating agents, antioxidants, and pH adjusters; and
- a pharmaceutically acceptable aqueous carrier, preferably purified water.

Preferably the composition is formulated for, or adapted for, application to the skin, coat, or hair of an animal.

There is also provided a method of treating insect bite allergic dermatitis in a mammal by topical application, preferably to the skin, coat or hair of the mammal, of a pharmaceutical composition as described herein to a mammal in need thereof.

DETAILED DESCRIPTION OF THE INVENTION

Definitions

Figure 1:
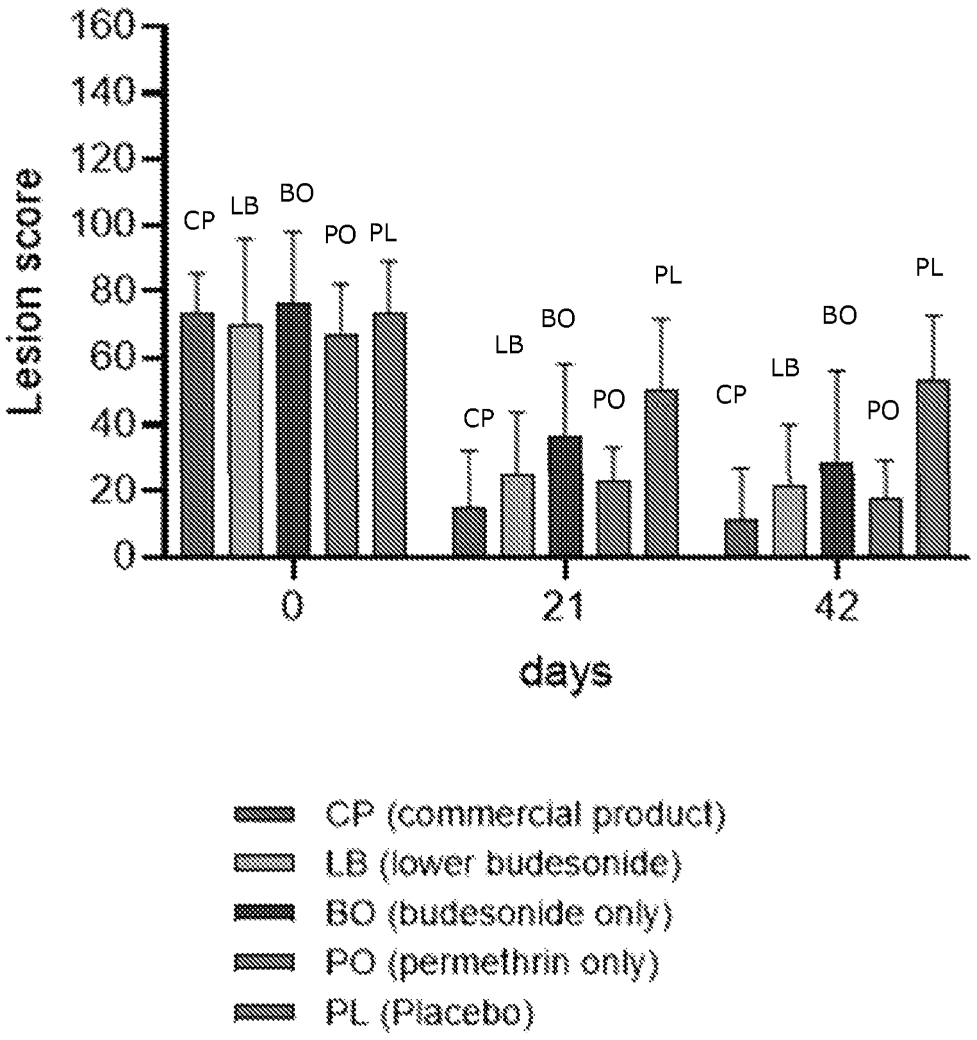
FIG. 1 is a graphical representation showing comparative mean lesion scores and standard deviations for each of the treatment groups in a randomized, controlled clinical study of a formulation of permethrin and budesonide for the topical treatment of horses suffering *Culicoides* allergy. Lesional scores in all treatment groups are shown at days 0, 21 and 42.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 10, 9, 8, 7, 6, 5, 4, 3, 2 or 1% to a reference quantity, level, value, number, frequency, percentage, dimension, size, amount, weight or length. The term "approximately" is construed similarly.

When used herein the terms "% w/w", "% w/v" and "% v/v" mean, respectively, weight to weight, weight to volume, and volume to volume percentages. Amounts stated as "g/L" means gram of component per litre of composition.

As used herein, the term "and/or" refers to and encompasses any and all possible combinations of one or more of the associated listed items, as well as the lack of combinations when interpreted in the alternative (or).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Thus, the use of the term "comprising" and the like indicates that the listed integers are required or mandatory, but that other integers are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

When used herein, the term "topical" when used in terms such as "topical application" "topical administration", "topical medication", "topical formulation" and the likes refer to application of a composition or formulation to body surfaces of the animal such as the skin, hair, coat or mucous membranes. In some preferred embodiments, the body surface is the skin, hair or coat of the animal.

When used herein the term "corticosteroid" refers to steroid anti-inflammatory pharmaceutical agents. Suitably the corticosteroid is adapted for topical application. Preferably the corticosteroid is a glucocorticoid. Suitably, the glucocorticoid is an approved or registered pharmaceutical suitable for animal use selected from, but not limited to, alclometasone; amcinonide; betamethasone; budesonide; clobetasol; clobetasone; desonide; desoximetasone; diflucortolone; diflorasone; fluocinolone; fluocinonide; flurandrenolide; fluticasone; halcinonide; halobetasol; halometasone; hydrocortisone; mometasone; methylprednisolone; triamcinolone; and or a salt, solvate and/or derivative of any one thereof. In some embodiments, the glucocorticoid is hydrocortisone or budesonide.

In one embodiment, the glucocorticoid is alclometasone dipropionate; amcinonide; betamethasone dipropionate; betamethasone valerate; budesonide; clobetasol propionate; clobetasone butyrate; desonide; desoximetasone; diflucortolone valerate; diflorasone diacetate; fluocinolone acetonide; fluocinonide; flurandrenolide; fluticasone propionate; halcinonide; halobetasol propionate; halometasone; hydrocortisone; hydrocortisone aceponate; hydrocortisone butyrate; hydrocortisone 17-butyrate; hydrocortisone valerate; mometasone furoate; methylprednisolone aceponate; or triamcinolone acetonide. In some embodiments, the glucocorticoid is budesonide.

When used herein, the term "pyrethrin" or "pyrethrin insecticide" refers to a natural pyrethrin compound extracted from the flowers of certain chrysanthemum species, notably *Chrysanthemum cinerariifolium*. The potent insecticidal activity of pyrethrins is achieved through their effect on the nervous system of insects. However, the skilled person will appreciate that the effectiveness of a pyrethrin insecticide may be due to its insecticidal and/or insect repellent properties. Both insecticidal and repellent effects of pyrethrins are encompassed herein. Examples of natural pyrethrins include pyrethrin I, pyrethrin II, cinerin I, cinerin II, jasmolin I and jasmolin II. Natural pyrethrins may be used individually or as a combination of two or more natural pyrethrins.

When used herein, the term "pyrethroid" or "pyrethroid insecticide" refers to a synthetic pyrethroid compound. Pyrethroids are synthetic versions of the natural pyrethrin structures and bear chemical modifications to increase stability and insect repellent and/or insecticidal efficacy. Pyrethroid compounds include, but are not limited to, allethrin I, allethrin II, bioallethrin, bifenthrin, permethrin, phenothrin, resmethrin, tefluthrin, and tetramethrin cyfluthrin, cyhalothrin, cypermethrin, deltamethrin, fenvalerate, fenpropathrin, flucythrinate, flumethrin, fluvalinate, and tralomethrin. In some embodiments, a pyrethroid insecticide is permethrin.

When used herein the term "silicone excipient" or "silicone" means a siloxane, and includes siloxanes such as cyclosiloxanes and polysiloxanes. Silicones are well known in the art and are readily available from commercial sources such as The Dow Chemical Co. Silicones are widely used in the formulation of pharmaceutical compositions, cosmetics and personal care products. Examples of silicones include, but are not limited to, at least one cyclosiloxane selected from cyclopentasiloxane and cyclotetrasiloxane, or a mixture thereof; and hydroxy terminated polydimethylsiloxane. In some embodiments, combinations of two or more silicones may be incorporated into a composition according to the invention in order to impart the desired physical properties to the composition. For example hydroxy terminated polydimethylsiloxane (dimethiconol, poly[oxy(dimethyl-silylene)], $\alpha$-hydro-$\omega$-hydroxy-) is a highly viscous siloxane which has emollient properties and can provide a soft silky feel and conditioning to the coat, hair or skin of the animal. Cyclosiloxanes, such as mixtures of cyclopentasiloxane and cyclotetrasiloxane provide spreading and lubrication properties. When used in the compositions described herein, the silicone mixtures can provide a conditioning effect on the animal's skin, coat or hair.

The term "insect bite allergic dermatitis" encompasses hypersensitivity reactions of an animal's skin to insect bites due to specific protein allergens in the insect's saliva. Insect bite allergic dermatitis may also be referred to as insect bite hypersensitivity (IBH). The condition is typically found in warm regions and can affect many species of mammals, such as domestic mammals including dogs and horses. Typically the insect may be a biting midge or flea, although it will be understood that the type of insect is not so limited. Typical biting insects include, for example, *Culicoides* spp. and *Ctenocephalides* spp., such as *C. felis* or *C. canis*. Other examples of biting insects include *Forcipomyia* spp., for example *Forcipomyia taiwana*. It will be appreciated that the species of biting insect will vary according to factors such as the specific geographical region or climate.

Insect bite allergic dermatitis in equines is usually caused by *Culicoides* spp. and is commonly known as *Culicoides* hypersensitivity allergic response. It is also known as seasonal recurrent dermatitis, Queensland Itch or Sweet Itch. Allergic reactions typically occur on the animal's skin at sites where the insects feed, for example the mane, tail and dorsal midline. Ventral symptoms may also occur. Lesions of skin around the ears, face and head are also commonly found.

In dogs, typical symptoms of insect bite allergic dermatitis include pruritic papular dermatitis on the animal's rump, dorsal thorax, flanks, tank or perineal area. Severe lesions include acral lick granuloma or pyotraumatic dermatitis.

Symptoms of insect bite allergic dermatitis may include, but are not limited to, one or more of dry, cracked or scaly skin; rash; redness; itching, including severe itching; swelling; burning; tenderness; sensitivity; lesions; papules or wheals which may accompanied by oozing or crusting; alopecia; excoriations; hypopigmentation; or and lichenification. A particularly troublesome symptom for the animal concerned are skin lesions accompanied by intense itching. This causes the animal to rub, often violently, with resultant self-trauma which may be considerable. This may cause damage to the coat, appearance of bald patches and broken bleeding skin. Secondary infections, such as bacterial or fungal infections, especially skin infections, may also occur. Common secondary bacterial infections include Staphylococcal infections.

When used herein, the term "derivative" includes chemical modifications introduced into the structure of a corticosteroid molecule. Typical derivatives of corticosteroids include derivatives of the steroid hydroxy substituents, for example esters, ethers and ketals, for example cyclic ketals such as acetonides. For example hydrocortisone may be derivatised to form an ester such as hydrocortisone aceponate, hydrocortisone butyrate, hydrocortisone 17-butyrate or hydrocortisone valerate. A corticosteroid molecule may be derivatised at one or more location.

Ester derivatives of corticosteroids are well known in the art. Typical ester derivatives of steroid hydroxy groups, particularly 17- or 21-hydroxy groups, include acetate, propionate, butyrate, valerate, pivalate, succinate, benzoate, salicylate and 2-furoate. Where a corticosteroid has two ester derivatives, examples include diacetate, dipropionate, divalerate, valeroacetate, acetate/propionate (aceponate), and butyrate and propionate (butyprate).

Cyclic ketals derivatives, such as acetonides, may be formed via two adjacent hydroxy groups on the steroid structure, for example 16- and 17-hydroxy substituents.

As used herein, the term "salts" and "solvate" include any pharmaceutically acceptable salt, or solvate of an active pharmaceutical ingredient. Pharmaceutically acceptable salts are well known in the art.

Salts of corticosteroids include sodium salts, including sodium salts of derivatives, for example sodium succinates.

Pharmaceutically acceptable solvates are known in the art, and include hydrates and alcoholates. Suitably, pharmaceutically acceptable solvates include hydrates, for example monohydrates, dihydrates and trihydrates.

The preparation of salts, derivatives and solvates can be carried out using methods well known in the art.

The chemical structures of corticosteroids or insecticides used in accordance with the invention may include asymmetric centres, such as asymmetric carbon atoms. It will be appreciated that the isomers arising from such asymmetry (e.g., all enantiomers, stereoisomers, diastereomers, rotomers or racemates) are included within the scope of this invention. Where stereochemistry is not specified, it will be understood that the structure is intended to encompass any stereoisomer and all mixtures thereof. For example, the corticosteroid budesonide [11β,21-dihydroxy-16α,17α-(butylidenebis(oxy))pregna-1,4-diene-3,20-dione, alternatively 1β,21-dihydroxy-16α,17α-[butane-1,1-diylbis(oxy)] pregna-1,4-diene-3,20-dione] can have (22R)- or (22S)-configuration.

The chemical structures of corticosteroids or insecticides used in accordance invention may include geometric isomers due to the presence of, for example, a carbon-carbon double bond. It will be appreciated that, unless otherwise stated, all geometric isomers, such as cis/trans geometric isomers, are included within the scope of this invention. Where stereochemistry is not specified, it will be understood that the structure is intended to encompass any geometric isomer and all mixtures thereof. Permethrin may exist as a cis- or trans-isomer or a mixture thereof, for example permethrin may be a 25:75 cis:trans mixture.

The term "subject", "individual", "mammal" or "animal" as used herein refers to a mammalian subject, for whom therapy or prophylaxis is desired. In particular embodiments, the subject is a domestic mammal, for example an equid including but not limited to horse, pony, donkey, ass, mule; a camelid including, but limited to, camel, llama, alpaca; dog; sheep; cattle; pig and goat. Preferably, the mammal is selected from cattle, pigs, sheep, dogs or horses. In some embodiments, the mammal is selected from cattle, pigs, sheep, goats, dogs or horses. In some embodiments, the mammal is a dog. In some embodiments, the mammal is an equine, for example a horse or pony. In some embodiments, the mammal is a goat.

The terms "alleviate", "treat", "treating", "inhibit" or "treatment" as used herein cover the treatment of insect bite allergic dermatitis and/or a symptom of insect bite allergic dermatitis and include: inhibiting the condition, i.e., arresting its development; relieving the condition, i.e., causing regression of the condition; or relieving the symptoms resulting from the condition without addressing the underlying disease or condition.

Each embodiment described herein is to be applied mutatis mutandis to each and every embodiment unless specifically stated otherwise.

Compositions of the Invention

The compositions of the invention find use in the treatment or inhibition of insect bite allergic dermatitis or symptoms associated with insect bite allergic dermatitis.

The present invention is based on the surprising discovery that a pharmaceutical composition formulated for topical application comprising a corticosteroid; an insecticide selected from a pyrethrin or a pyrethroid; and a pharmaceutically acceptable carrier provides access to an effective and convenient treatment for insect bite allergic dermatitis.

The pharmaceutical compositions described herein comprise a combination of an insecticidal or insect repellent agent with a corticosteroid anti-inflammatory agent. The components are readily available and provide a cost effective treatment for insect bite allergic dermatitis. In preferred embodiments, the compositions comprise a topical corticosteroid, such as hydrocortisone or budesonide. These topical corticosteroids are largely metabolised in the skin and as little as 0.4 to 0.7% becomes systemic, thus minimising the potential for any systemic side effects such as those typically encountered with systemic corticosteroids. In some embodiments, the topical steroid is a "soft" or "dissociative" steroid. These steroids are androstene-derived steroids which exhibit anti-inflammatory effects similar to those of conventional corticosteroids but without the potentially serious systemic side effects associated with some conventional steroids.

In preferred embodiments, the corticosteroid is a glucocorticoid suitable for topical application. In some embodiments, the glucocorticoid is selected from glucocorticoids that, when applied to the skin of a mammal, are not substantially absorbed systemically. Preferred glucocorticoids are those which are substantially metabolized in the skin, thus reducing or minimizing any undesirable systemic effects. Examples of suitable glucocorticoids are well known in the art. In some embodiments, the glucocorticoid is selected from alclometasone; amcinonide; betamethasone; budesonide; clobetasol; clobetasone; desonide; desoximetasone; diflucortolone; diflorasone; fluocinolone; fluocinonide; flurandrenolide; fluticasone; halcinonide; halobetasol; halometasone; hydrocortisone; mometasone; methylprednisolone; triamcinolone; and or a salt, solvate and/or derivative of any one thereof. In some embodiments, the corticosteroid is hydrocortisone or a salt and/or solvate and/or derivative thereof, for example hydrocortisone aceponate. In some particular embodiments, the corticosteroid is budesonide or a salt and/or solvate and/or derivative thereof.

In some embodiments, the insecticide is a natural pyrethrin insecticide such pyrethrin I, pyrethrin II, cinerin I, cinerin II, jasmolin I or jasmolin II, or a mixture of two or more thereof. Pyrethrins are extracted from the dried flowers of certain chrysanthemum species, notably *Chrysanthemum cinerariifolium*, which is grown commercially in, for example, Kenya. Isolated pyrethrins are readily obtainable from commercial sources.

In some embodiments, the insecticide is a synthetic pyrethroid insecticide. Synthetic pyrethroid insecticides are well known in the art and are commercially available. It will be appreciated that the pyrethroid compound is suitable for application to the skin of an animal. Pyrethroid insecticides include, but are not limited to, allethrin I, allethrin II, bioallethrin, bifenthrin, permethrin, phenothrin, resmethrin, tefluthrin, and tetramethrin cyfluthrin, cyhalothrin, cypermethrin, deltamethrin, fenvalerate, fenpropathrin, flucythrinate, flumethrin, fluvalinate, and tralomethrin. In some embodiments, the pyrethroid insecticide is permethrin. Permethrin exists in the form of cis- and trans-geometric isomers. In compositions described herein, permethrin may comprise a single geometric isomer, or may comprise both isomers as a mixture. In some embodiments, the permethrin is a mixture of cis- and trans-isomers in about a 25:75 ratio.

The amount of corticosteroid present in the composition will depend on the type of formulation and how it is to be applied. For example, typically an ointment, cream, lotion, conditioner, leave-in (or leave on) conditioner, pour-on or spray formulation may comprise a corticosteroid in an amount of from about 0.025 g/L to about 0.5 g/L or from about 0.025 g/L to about 1 g/L; about 0.05 g/L to about 0.5 g/L or about 0.05 g/L to about 1 g/L; or about 0.1 g/L to about 0.5 g/L or about 0.05 g/L to about 1 g/L; for example from about 0.05 g/L to about 0.6 or 0.8 g/L, or from about 0.1 g/L to about 0.5 g/L; from about 0.15 g/L to about 0.5 g/L; from about 0.1 g/L or 0.15 g/L to about 0.4 g/L; about 0.2 g/L to about 0.4 g/L; about 0.1 g/L to about 0.3 g/L; about 0.15 g/L to about 0.5 g/L; about 0.2 g/L to about 0.5 g/L; about 0.15 g/L to about 0.35 g/L; about 0.15 g/L to about 0.45 g/L; about 0.2 g/L to about 0.4 g/L; about 0.25 g/L to about 0.5 g/L; about 0.25 g/L to about 0.4 g/L; about 0.2 g/L to about 0.3 g/L; and especially about 0.25 g/L. It will be appreciated that if the application of the composition involves rinsing, such as a shampoo or wash formulation, this may require a greater concentration of corticosteroid.

The amount of insecticide present in the composition will depend on the type of formulation and the method of application. Typically the formulation may comprise a pyrethrin or pyrethroid insecticide in an amount of from about 0.5 g/L to about 60 g/L, about 0.5 g/L to about 50 g/L, or about 1 g/L to about 50 g/L; for example from about 5 g/L to about 50 g/L, about 10 g/L to about 45 g/L, about 20 g/L to about 40 g/L, about 30 g/L to about 45 g/L or from about 35 g/L to about 45 g/L, and especially about 40 g/L. In some embodiments, the composition comprises a pyrethrin or pyrethroid insecticide in an amount of up to 10, 15, 20, 25, 30, 35, 40 or 45 g/L. In some embodiments, the composition comprises a pyrethrin or pyrethroid insecticide in an amount of at least 5, 10, 15, 20, 25, 30, or 35 g/L. It will be appreciated that if the application of the composition involves rinsing, such as a shampoo or wash formulation, this may require a greater concentration of insecticide.

In some embodiments, the corticosteroid is present in a composition of the invention in an amount of about 0.0025% w/w to about 0.1% w/w. In some embodiments, the corticosteroid is present in an amount of about 0.005% w/w to about 0.1% w/w; about 0.0075% w/w to about 0.1% w/w; about 0.01% w/w to about 0.075% w/w; about 0.01% w/w to about 0.05% w/w; about 0.02% w/w to about 0.04% w/w; about 0.02% w/w to about 0.3% w/w; or about 0.025% w/w. In some embodiments, the corticosteroid is present in about 0.015% w/w to about 0.05% w/w; about 0.02% w/w to about 0.05% w/w; about 0.015% w/w to about 0.035% w/w; about 0.015% w/w to about 0.045% w/w; about 0.02% w/w to about 0.04% w/w; about 0.025% w/w to about 0.05% w/w; about 0.025% w/w to about 0.04% w/w; about 0.02% w/w to about 0.03% w/w; and especially about 0.025% w/w.

In some embodiments, the insecticide is present in a composition of the invention in an amount of about 0.05% w/w to about 5.0% w/w. In some embodiments, the insecticide is present in an amount of about 0.1% w/w to about 4.5% w/w; about 0.15% w/w to about 4% w/w; about 0.2% w/w to about 4% w/w; about 0.5% w/w to about 4.5% w/w; about 1% w/w to about 4% w/w; 2% w/w to about 4.5% w/w; or about 4% w/w.

In some embodiments, the ratio of corticosteroid to a pyrethrin or pyrethroid insecticide is from about 1:100 to about 1:200 by weight, for example about 1:125 to about 1:175 by weight or about 1:140 to about 1:170 by weight. In some embodiments, the ratio of corticosteroid to pyrethrin or pyrethroid insecticide is about 1:160 by weight.

When a composition of the invention includes one or more silicones, it will be appreciated that the amount of silicone components present will depend on the type of formulation and how it is to be applied. In some compositions as described herein, such as lotions or leave-in conditioners, the ratio of APIs (insecticide and corticosteroid) to combined amount of silicones is about 1:2 to 2:1 or about 1:2 to 3:2, for example about 40:70 or 41:75.

In its simplest form, the composition of the invention may comprise a corticosteroid; an insecticide selected from pyrethrin insecticides and pyrethroid insecticides; and a pharmaceutically acceptable carrier. The skilled person will appreciate that the composition may also include other pharmaceutically acceptable additives, such as surfactants, emulsifiers, rheology or viscosity modifiers, solvents or solubilizing agents, buffering agents, pH adjusters, diluents, dispersing agents, chelating agents, preservatives, antioxidants, stabilisers, tonicity agents, humectants, thickening agents and excipients.

The compositions preferably comprise one or more silicones as conditioning excipients.

The inventor has discovered that compositions of the invention further comprising one or more silicones are particularly advantageous. Silicones provide properties such as film forming properties, wash-off resistance and spreadability to a composition. Silicones can also provide soothing and emollient properties and can thus provide a soothing effect on the skin, or a conditioning of the skin, coat or hair of the animal. In some embodiments, the presence of one or more silicones in a composition of the invention provides an emollient effect. This emollient effect may be due to formation of a residual layer or film of silicone on the animal's skin which forms a barrier to repel water (see, e.g., https://luisafanzani.com/what-is-dimethicone/).

Accordingly, in a further aspect, the present invention advantageously provides a pharmaceutical composition for topical application comprising, consisting of, or consisting essentially of:

- a corticosteroid;
- a pyrethrin insecticide or pyrethroid insecticide;
- one or more silicones; and
- a pharmaceutically acceptable aqueous carrier; and, optionally
- one or more pharmaceutically acceptable excipients.

In some embodiments, the one or more silicones are present in a composition in an amount of from about 25 g/L to about 150 g/L, for example about 50 g/L to about 100 g/L, about 60 g/L to about 90 g/L, about 70 g/L to about 80 g/L, or about 75 g/L.

In some preferred embodiments, the silicone-containing composition is formulated as a conditioner, leave-in conditioner or a lotion. Suitably, the composition is packaged in a pump dispenser which is adapted to deliver a pre-determined amount of composition per actuation. In some embodiments, the composition of the invention is a leave-in conditioner formulation, also referred to a leave on conditioner, for application to the skin, coat or hair of the animal comprising one or more silicones.

The skilled person will appreciate that the physical properties of silicones will vary in accordance with their chemical structure and will be able to select appropriate silicones in accordance with the desired final physical properties of the composition. Suitable silicones are well known in the art and one or more silicones may be selected to confer properties such as increased or reduced viscosity, film forming properties, wash-off resistance, spreadability, volatility or permeability to a composition. The amount and type of silicone(s) present in a composition of the invention may be adjusted according to the needs of the animal and will depend on the species, for example dog or horse. It will be appreciated that factors such as the type of animal, the disease state and chronicity, coat length, oiliness and general condition of skin or hair may be taken into account in formulating a composition.

In some embodiments, the composition comprises one or more silicones selected from cyclopentasiloxane, cyclotetrasiloxane and hydroxyl terminated polydimethylsiloxane. In some embodiments, combinations of two or more silicones may be incorporated into the composition according to the invention in order to impart the desired physical properties. In some examples, the composition comprises cyclopentasiloxane, cyclotetrasiloxane and hydroxy terminated polydimethylsiloxane. Suitable silicones and silicone mixtures are readily obtainable from commercial sources. Examples include Xiameter® PMX-0344 or Xiameter® PMX-1401 available from The Dow Chemical Company. Xiameter® PMX-0344 is a cyclosiloxane blend comprising cyclopentasiloxane and cyclotetrasiloxane. This silicone mixture can act as a base fluid and has good spreading and lubrication properties and unique volatility characteristics. Xiameter® PMX-1401 is a 13% solution of blend of dimethiconol (hydroxyl terminated polydimethylsiloxane) in cyclopentasiloxane and cyclotetrasiloxane. The hydroxyl terminated polydimethylsiloxane can act as an emollient and thus can provide a soft feel to the skin and condition the hair and coat.

Dimethiconol is a highly viscous polysiloxane silicone. In some embodiments of the invention, dimethiconol is present in a composition of the invention in an amount of about 0.5 g/L to 3 g/L; for example from about 1 g/L to 2.5 g/L; or about 2 g/L; or about 1.95 g/L.

Cyclosiloxanes comprising a mixture of cyclopentasiloxane and cyclotetrasiloxane may be present in a composition in an amount of about 25 g/L to about 125 g/L; for example from about 50 g/L to about 100 g/L; 60 g/L to about 80 g/L; or about 70 g/L to 75 g/L; for example about 73%.

In yet another aspect, there is provided a pharmaceutical composition formulated for topical administration comprising, consisting of, or consisting essentially of:

a corticosteroid in an amount of about 0.025 g/L to about 1 g/L, a pyrethrin insecticide or a pyrethroid insecticide in an amount of about 0.5 g/L to about 50 g/L;

one or more cyclosiloxanes in an amount of about 25 g/L to about 150 g/L, for example about 50 g/L to about 100 g/L;

At least one polysiloxane, such as dimethiconol, in an amount of about 1 g/L to about 3 g/L, for example about 2 g/L.

at least one pharmaceutically acceptable excipient; and a pharmaceutically acceptable aqueous carrier.

Topical administration according to the invention may be by means of any formulation suitable for delivering the active ingredients to the skin or coat of the animal. Topical formulations are well known in the art and are described in, for example, Ueda et al., Topical and Transdermal Drug Products, Pharmacopeial Forum, Vol. 35(3), 2009; Buhse et al., Topical Drug Classification, International Journal of Pharmaceutics, 2005, 295, 101-112. Suitable formulations include, but are not limited to, liquids, aerosols, creams, ointments, lotions, mousses, gels, shampoos, conditioners and leave-in conditioners. In some embodiments, the pharmaceutically acceptable carrier is an aqueous carrier, for example water, such as purified water.

In some embodiments, the composition is a liquid such as an aqueous liquid or aqueous solution. Liquids may be applied to the coat or skin of the animal by any suitable means, for example as a lavage, drench, dip, spray, aerosol, pour-on, or backliner. The liquid may be a ready to use formulation or may be supplied as a concentrate to be diluted with an aqueous diluent such as water prior to application. The concentration of the composition will depend on the intended method of administration. For example, a composition for spray, dip, drench, lavage or pour over may be a more dilute formulation than a composition to be applied as a pour-on or spray on backliner. Backliners are ready to use liquid formulations that may be applied to animals, such as cattle, sheep, pigs or horses, by pouring it along the backline from the neck to tail. In some embodiments, the composition may be formulated as a spray-on for administration by spray, such as that delivered by a trigger spray bottle. Other suitable means of application are known in the art, for example, a moistened gauze, swab, cotton, foam, sponge or cloth. In some examples, the composition may be applied by hand to the skin or coat.

In some embodiments, the composition of the invention is a cream or lotion. Creams are semi-solid multi-phase compositions containing the active agents, in this case the corticosteroid and insecticide, each dissolved in a suitable base. Creams include water-in-oil or oil-in-water emulsions, or aqueous microcrystalline dispersions of long-chain fatty acids or alcohols, and generally have a relatively soft, spreadable consistency.

In some preferred embodiments, the composition is in the form of a lotion. Lotions share many characteristic with creams and are typically a viscous emulsion, solution or suspension. Typically they contain an aqueous vehicle and more than 50% water and volatiles. Lotions are easy to apply and, being water based, they are easy to remove. They can have an emollient effect and can leave a cooling or soothing sensation on the animal's skin.

In some embodiments, where the composition is to be topically applied to skin bearing hair, the composition may be in the form of a shampoo or conditioner. Conditioners, such as hair conditioners are well known with respect to hair care. Such conditioner formulations are particularly useful for application to parts of an animal's body bearing hair.

The inventor has discovered that conditioning compositions are useful formulations for the compositions of the invention. The inventor has also identified that compositions of the invention formulated as a leave-in (also referred to as a leave on) conditioner are particularly advantageous. A leave-in conditioner is a conditioning product that may be applied to hair, skin or coat of the animal. Leave-in conditioners generally include silicones. Such conditioner formulation bases and excipients are well known and are described in, for example Barel et al., Handbook of Cosmetic Science and Technology, Third Edition, 2009. CRC Press. page 687.

The presence of silicones in leave-in conditioners of the present invention provide a conditioning and emollient effect due to the provision of water repellence by forming a residual film or barrier on the coat of the animal. Leave-in conditioners allow penetration of the pelage and coat the hair with a residual film of medication. The leave-in conditioners of the present invention demonstrate several advantages over other forms of topical applications. For example, the application of a spray formulation may frighten or stress an already distressed animal, particularly a horse. Semi-solid dosage forms such as creams require massage to penetrate the coat. Massaging the sensitive skin is generally objected to by the animal and the massaging action can cause matting of the coat and prevent proper spreading and application of the cream.

Leave-in conditioner formulations are lighter and less viscous than standard conditioners and provide a thin residual layer of the formulation on the coat, hair or skin of the animal. In their simplest form, leave—in conditioners can be used to restore lost moisture to skin and hair. In the compositions of the invention, in addition to treating the symptoms of IBH, leave-in conditioners provide a conditioning and/or emollient effect due to the residual film which may provide water repellence. This is advantageous, since exposure of the skin lesions to water can aggravate the suffering of the animal. The conditioner may be applied to an animal's coat at any time, however it is preferably applied to a freshly cleansed animal coat. The coat may be dry, damp or wet; but preferably the animal's coat is damp.

Leave-in conditioner formulations of the present invention are easy and quick to apply and limit the amount of discomfort or stress to the animal. They provide rapid relief. They are cost effective and long lasting, thus do not require frequent re-application.

Lotions and leave-in conditioners are suitably dispensed from a pump dispenser which may be adapted to dispense a pre-determined dosage and amount of the composition. In some examples, a pump is adapted to dispense about 1.6 mL or 1.5 g of a lotion or leave-in conditioner per actuation.

The compositions of the invention may be prepared by conventional methods well known in the art. Typically the desired ingredients are measured by weight or volume, as appropriate, and combined to form a substantially homogeneous mixture using a mixing technique such as milling, blending, shear mixing, or homogenizing in a suitable vessel. The person of ordinary skill will be able to determine the most suitable mixing technique and vessel according to the batch size and physical form of the starting materials and the final composition. Preferably the APIs, carriers and excipients are combined in a homogenizer. The selection of additional excipients, if desired or required, is well within the knowledge of the skilled person, and will depend on considerations such as the type and physical form of composition required.

The composition is formulated as a composition adapted for, or suitable for, topical administration. Preferably the pharmaceutical composition is an aqueous formulation. It will be appreciated that any carriers and excipients used must be "acceptable" in the sense of being compatible with the other ingredients of the composition and not deleterious to the recipient thereof. In some embodiments, the aqueous carrier is purified water. It will also be understood that a composition for topical application is preferably of a physiologically acceptable pH. Preferably the composition has a final pH of 3.5-4.5.

The pharmaceutical compositions of the present invention, or the compositions used in the methods of the present invention, may be formulated and administered using methods well known in the art. Techniques for formulation and administration may be found in, for example, *Remington: The Science and Practice of Pharmacy*, Loyd V. Allen, Jr (Ed), The Pharmaceutical Press, London, 22nd Edition, September 2012.

It will be understood that it may be useful to incorporate one or more pharmaceutically acceptable excipients in the composition. Excipients for aqueous compositions include, but are not limited to, buffers, stabilizers, chelating agents, tonicity agents, humectants, antioxidants, thickening agents, solubilizing agents, viscosity modifiers, rheology modifiers, and preservatives. Suitable excipients are well known in the art and are readily available from commercial sources. Preferably, the excipients are of pharmaceutical grade, for example USP or BP grade. Pharmaceutical excipients are described in, for example, *Handbook of Pharmaceutical Excipients*, Paul J. Sheskey et al., The Pharmaceutical Press, London, Eighth Edition, August 2017. It will be appreciated that determination of whether a particular class of excipient is required, and selection of an appropriate excipient will be well within the skill and knowledge of a person of ordinary skill. It will also be recognized that an excipient must be chemically inert with respect to the other components in the composition. The concentration of any particular excipient will vary in accordance with its identity and the skilled person would readily be able to select suitable excipients and determine the amount necessary without undue burden or inventive input.

For example, excipients may include one or more pH adjusters or buffering agents to adjust the pH of the composition to a physiologically acceptable pH or to maintain the pH of the composition at a physiologically acceptable pH. Suitable buffering agents are well known in the art. Suitable pH adjusters include acids, such as hydrochloric acid; or bases or alkalis, such as sodium or potassium hydroxide.

In some embodiments, it may be beneficial to solubilize certain components when preparing a composition as described herein. For example, it will be appreciated that it may be useful to solubilize a corticosteroid or an insecticide in a non-aqueous solvent prior to, or concomitant with, introduction into an aqueous base during the preparation of a pharmaceutical composition as described herein. Suitable solvents, co-solvents or solubilizing agents for organic APIs, such as corticosteroids and insecticides, are well known in the art. The skilled person would be readily able to decide if use of a solvent/solubilizing agent is desirable or necessary. The selection of particular solubilizing agents or solvents, or classes of solubilizing agents or solvents, and the determination of the amount of a solubilizing agent or solvent will be well within the skill and knowledge of a person of ordinary skill. In some embodiments, solubilizing agents include oleoyl macrogel-6 glycerides. In some embodiments, solubilizing agents include N-methylpyrrolidone (NMP), propylene glycol, or 2-(2-ethoxyethoxy)ethanol. It will be appreciated that the amount and selection of solubilizing agents required will depend on the solubility characteristics of the APIs and their concentration in the aqueous composition. The person of ordinary skill can readily determine this based on general knowledge and the examples herein without inventive input. Solubilizing agents may be present in a composition of the invention in an amount of, for example, from about 100 g/L to about 200 g/L; or about 150 g/L or about 130 g/L.

Surfactants, such as non-ionic water dispersible surfactants, are well known in the art of pharmaceutical formulation. These can solubilize and increase bioavailability of poorly water-soluble active pharmaceutical ingredients (APIs). They can also act as a co-emulsifier in topical formulations to improve stability of emulsions. An example of a non-ionic water dispersible surfactant is oleoyl macrogel-6 glycerides available as Labrafil® M 1944. Such a surfactant may be present in a composition of the invention an amount of about 10 g/L to about 30 g/L for example, about 20 g/L.

The skilled person will also appreciate that thickening agents, rheology modifiers or viscosity modifiers may be incorporated into the composition to adjust the viscosity or rheology properties to the requirements for topical application. Suitable thickening agents are well known in the art and include derivatives of cellulose, such as hydroxypropyl methyl cellulose, carboxymethyl cellulose; natural gums, such as sodium alginate, xanthan, agar or carrageenan; pectins; and gelatin. If present, the amount of thickening agent in a composition of the invention will depend on the desired consistency.

Thickening, stabilizing and emulsifying agents or excipients for products formulated as lotions or leave-in conditioners are well known in the art. These excipients are useful as they can provide an advantageous base for the compositions of the invention that can condition the animal's coat or condition or soothe the animal's skin. In preferred embodiments, a composition of the invention comprises one or more excipients selected from thickening, stabilizing and emulsifying agents. Suitable excipients for the formulation of cosmetic, hair care, personal care and pharmaceutical compositions are well known. One such excipient is a commercially available thickener/stabilizer/emulsifier combination comprising polyquaternium-37, propylene glycol dicaprate dicaprylate and PPG-1 Trideceth-6 available commercially from BASF as Salcare®SC96. In some preferred embodiments, the compositions comprise one or more conditioning excipients. In some embodiments, the thickener/stabilizer/emulsifier is present in an amount of about 10 g/L to about 60 g/L, for example about 20 g/L to about 40 g/L, or about 30 g/L.

In some embodiments, the composition comprises a corticosteroid in an amount of about 0.025 g/L to about 1 g/L; an insecticide selected from a pyrethrin or a pyrethroid in an amount of about 0.5 g/L to about 60 g/L; and thickening, stabilizing and emulsifying agents totaling about 10 g/L to about 60 g/L; a pharmaceutically acceptable carrier; and optionally one or more silicones totaling about 25 g/L to about 150 g/L.

In a preferred embodiment, the composition comprises one or more silicones and one or more thickening agents. In some embodiments, the ratio of silicones to thickening agents is from about 4:1 to 3:2, or 3:1 to 2:1; for example, about 75:30. The combined amount of thickening agent and silicones in the composition forms typically about 10-12% of the formulation by weight. In some embodiments, the combined amount of silicones and thickening agents present in the formulation is 100 g/L to 200 g/L.

The skilled person will recognize that a composition of the invention may be susceptible to microbial contamination or physical or chemical degradation, accordingly a preservative may be incorporated into the composition to reduce or avoid its degradation or alteration. Suitable preservatives and anti-oxidants are well known in the art and the selection of particular preservatives or anti-oxidants and the determination of the amount required will be well within the skill and knowledge of a person of ordinary skill. In some embodiments, an anti-oxidant is butylated hydroxy toluene, for example in an amount of about 0.2 g/L to about 1 g/L, such as 0.5 g/L. Preservatives are well known in the art, and include one or more of propylene glycol, diazolidinyl urea and parabens such as methyl paraben and propyl paraben. Typical amounts of preservatives in a composition as described herein are about 5 g/L to about 15 g/L, for example about 10 g/L. Preservatives for pharmaceutical and personal care formulations are commercially available. One example is a mixture propylene glycol, diazolidinyl urea, methyl paraben and propyl paraben, available commercially as Germaben II®.

A composition of the invention may also include one or more stabilizers. Examples of stabilizers include chelating agents such as ethylenedinitrilotetraacetic acid disodium salt dihydrate. The amount of stabilizer used will depend on the circumstances, for example amounts of about 0.5 g/L to about 2 g/L is envisaged, for example about 1 g/L.

In a particular embodiment, the present invention provides a leave-in conditioner formulation comprising, consisting of, or consisting essentially of:

budesonide: about 0.25 g/L;
permethrin: about 40 g/L;
silicones, for example, one or more of cyclopentasiloxane, cyclotetrasiloxane and hydroxyl terminated polydimethylsiloxane in a total amount of about 75 g/L;
thickening agents, for example a mixture of Polyquaternium-37/propylene glycol dicaprate dicaprylate/PPG-1 Trideceth-6, in an amount of about 30 g/L;
oleoyl macrogel-6 glycerides: about 20 g/L;
N-methylpyrolidone: about 50 g/L;
propylene glycol: about 30 g/L
2-(2-ethoxyethoxy)ethanol: about 50 g/L
one or more pharmaceutically acceptable excipients selected from chelating agents, stabilizers, antioxidants, preservatives and pH adjusters; and
purified water (to 1000 mL).

In some preferred embodiments, the silicones comprise cyclosiloxanes, for example, one or more of cyclopentasiloxane and cyclotetrasiloxane, in an amount of about 73 g/L; and hydroxyl terminated polydimethylsiloxane in a total amount of about 2 g/L or 1.95 g/L.

If desired, the compositions of the invention may further comprise one or more physiologically active agents. Preferably, any additional physiologically active agents may be formulated as a topical formulation. Additional therapeutically active ingredients may include antibiotics. Other therapeutically active ingredients include analgesics, anti-inflammatory or antipyretic agents.

Methods of the Invention

The compositions described above find use in methods of treating insect bite allergic dermatitis.

Accordingly, there is also provided a method of treating insect bite allergic dermatitis or a symptom thereof in a mammal comprising administering to the mammal an effective amount of a pharmaceutical composition as described herein.

Preferably, the mammal is selected from cattle, pigs, sheep, dogs and equines. In some embodiments, the mammal is a dog. In some embodiments, the mammal is an equine, such as a horse or pony. In some embodiments, the mammal is a goat.

In a further aspect, there is provided a pharmaceutical composition as described herein for use in treatment of insect bite allergic dermatitis or a symptom thereof. There is also provided a pharmaceutical composition as described herein for use in therapy. The pharmaceutical composition as described herein may also be used in the manufacture of a medicament for treatment of insect bite allergic dermatitis or a symptom thereof.

Although other modes of administration may be contemplated, the compositions of the invention are primarily intended for topical administration to the skin, coat or hair of the animal. In the methods or uses described herein, the composition of the invention is delivered topically.

It will be understood that a composition of the invention will be most effective when it is applied such that it contacts the skin, particularly in areas typically affected by insect bite allergic dermatitis. Queensland Itch lesions are consistent with the insects preferred feeding sites, for an equine, the composition is typically applied as required to the coat or skin in one or more of the backline, mane, tail, ears, head, dorsal midline or ventral areas of the equine. In some examples, the composition is suitably applied to one or more of the dorsal areas, such as the forehead, poll, ears, neck, crest, withers, shoulders or rump, as required. For a canine, the composition is typically applied to one or more of the rump, dorsal thorax, flanks, tanks or perineal area of the dog.

In some examples, the composition of the invention is hand spread on the animal's coat, suitably using a circular motion.

It will be appreciated that a composition as described herein is likely to be more effective if applied to a clean animal coat. In the case of a leave-in conditioner, pour-on, spray or lotion formulation, preferably the animal's coat is freshly cleansed and damp.

It will be appreciated that there will be variation in how far a dose of composition will spread on an animal. A formulation as described herein when spread on the coat may disperse considerably in the hair before reaching the skin. This varies according to the animal species, e.g. dog, horse. It will also depend on such factors as the length of the hair; the density of coat; the texture of the hair (coarse/fine); the amount of sebum/scale present on the skin surface and the oiliness of the coat. Furthermore, coat density varies on different parts of the body, with the coat tending to be finer on the shoulder and more dense on the rump, tail and mane areas. Thus depending on the circumstances, it will be appreciated that the product may be diluted depending on the method of application. It will be appreciated that it may be necessary to adjust the amount and type of excipients and the amount of carrier present in the formulation to enable optimum delivery to the animal's skin. For example, a spray application may be diluted with water.

A composition of the invention may be used in any amount that is effective to inhibit or treat insect bite allergic dermatitis. As used herein, the term "effective amount" relates to an amount of the composition which, when administered according to a desired dosing regimen, provides the desired therapeutic activity for the condition. Typically, dosing may occur at intervals of hours, days, weeks or months. Weekly application of a composition of the invention is considered adequate. A therapeutic effective amount or treatment effective amount is an amount of the composition, which when administered according to a desired dosage regimen, is sufficient to at least partially attain the desired therapeutic effect, or delay the onset of, or inhibit the progression of, halt, partially or fully the onset or progression of the condition. A preventative effective amount of the composition, which when administered according to a desired dosage regimen, is sufficient to at least partially prevent the onset of the condition.

The dosage and frequency of administration of the composition will depend on the requirements of the particular mammal to be treated. Suitable dosage amounts and dosing regimens may be determined by the veterinarian and may depend on the severity of the condition as well as the general age, health and weight of the mammal being treated.

In some examples, a lotion or leave-in conditioner according to the invention can be applied at around 1 g or about 1.5 g (about 1.5 mL, e.g. 1.6 mL), to cover approximately 0.025 to $0.03M^2$ of the mammal's skin. In some examples, a pump is adapted to dispense about 1.6 mL of a lotion or leave-in conditioner. This can typically cover about $0.025M^2$ (about a handspan) when hand spread on an animal's coat. In some examples of the invention, this may contain about 0.0004 g of corticosteroid, 0.064 g of insecticide, or about 0.0004 g of corticosteroid, 0.064 g of insecticide and 0.12 g of silicones.

In some embodiments of the invention, the composition is applied approximately weekly.

Those skilled in the art will appreciate that the invention described herein is susceptible to variations and modifications other than those specifically described. It is to be understood that the invention includes all such variations and modifications which fall within the spirit and scope.

In order that the invention may be readily understood and put into practical effect, particular preferred embodiments will now be described by way of the following non-limiting examples.

EXAMPLES

Compositions of the invention can be prepared from commercially available active pharmaceutical ingredients, carriers and excipients. The compositions may be prepared using conventional routes for the preparation of pharmaceutical formulations using conventional equipment for mixing, such as a blender, mixer or homogenizer.

Example 1

Preparation of Pharmaceutical Composition (IVP)

The following commercially available ingredients were combined with mixing in a homogenizer:

budesonide [corticosteroid; 0.25 g];
permethrin [insecticide; 25:75 cis:trans; 40 g];
cyclotetrasiloxane/cyclopentasiloxane mixture (Xiameter® PMX-0344) [silicone excipient/conditioner; 60 g];
13% solution of hydroxy terminated polydimethylsiloxane in cyclopentasiloxane and cyclotetrasiloxane (Xiameter® PMX-1401) [viscous silicone conditioner, 15 g];
Polyquaternium-37/propylene glycol dicaprate dicaprylate/PPG-1 Trideceth-6 (Salcare® SC96) [thickening agent; 30 g];
oleoyl macrogel-6 glycerides (Labrafil® M 1944) [solubilizing agent, surfactant; 20 g];
ethylenedinitrilotetraacetic acid disodium salt, dehydrate [chelating agent; 1 g];
N-methylpyrrolidone [solubilizing agent; 50 g];
propylene glycol [solubilizing agent; 30 g];
2-(2-ethoxyethoxy)ethanol [solubilizing agent; 50 g];
butylated hydroxy toluene [antioxidant; 0.5 g];
propylene glycol/diazolidinyl urea/methyl paraben/propyl paraben (Germaben II) [preservatives, 10 g];
purified water [to 1000 g];
pH modifiers (hydrochloric acid, sodium hydroxide) to pH 3.5-4.5.

The formulated composition, referred to as CP or the Formulation of Example 1, is suitable as a leave in conditioner. It was introduced into a pump action dispenser adapted to dispense a pre-determined volume of composition per actuation. The pump typically dispenses 1.5 g or about 1.6 mL per actuation.

Example 2

Efficacy Studies

Clinical studies were carried out using the formulation of Example 1 in horses suffering from Queensland Itch. Thus, horses suffering *Culicoides* allergy were treated topically in a blinded trial carried out to Good Clinical Practices standard in accordance with *GCP International Cooperation on Harmonisation of Technical Requirements for Registration of Veterinary Medicinal Products* (*VICH*) *Guideline* 9', 15 Jun. 2000. This randomized, placebo-controlled study investigated the efficacy of the leave on conditioner of Example 1 (CP) containing budesonide and permethrin, which was aimed to treat culidoides hypersensitivity (Queensland Itch, sweet itch, QI) in horses. CP has two active ingredients, budesonide (steroid alleviating itch and inflammation) and permethrin (insect repellent). Horses were treated with commercial product (CP), Placebo (control, excipients only, PL) and three comparative products that had variable levels of active ingredients. Lower budesonide (LB) had 50% less budesonide than CP, but the same amount of permethrin.

Budesonide only (BO) and permethrin only (PO) had only single active ingredient in the same amount as CP, to show the effect of that active alone.

The data from 51 horses (10 horses per group except 11 in budesonide only) with naturally occurring Queensland Itch was collected and analyzed. Each horse received 40 pumps (approximately 60 grams) on the skin weekly for 6 weeks. Each dose was administered by a veterinarian on areas where QI generally occurs, i.e. face, head, neck, flanks and back. The veterinarian performed assessment on horses at days 0, 21 and 42 and owners measured itch and quality of life scores. Statistical analysis was performed with GraphPad Prism 8 Software. Non-parametric One-way ANOVA (Kruskal-Wallis test with Dunn's multiple comparisons) was used.

Lesion Scores: Lesion scores were calculated from four different components, excoriations, scale and crust, alopecia and papules. These are most common lesional types in horses suffering from QI. The scores were calculated at 8 different sites on the horses' body. At each of the eight sites, the severity of each sign was graded from 0 (none) to 5 (severe). The total lesion score was then calculated by the (severity)×(numbers of signs)×(sites), leading to a total possible maximum score of 160. Each horse was assigned a score on day 0, day 21 and day 42. FIG. 1 shows the lesion scores in all treatment groups at days 0, 21 and 42, which was the endpoint of the study.

Total lesion scores (maximum score 160) were similar between groups at baseline ($p=0.6259$). At day 21 only CP ($p=0.0012$) and at day 42 both CP and PO were significantly different from Placebo ($p=0.0003$ and $p=0.0366$, respectively). Multiple comparison showed no other differences between treatment groups.

Figure 2:
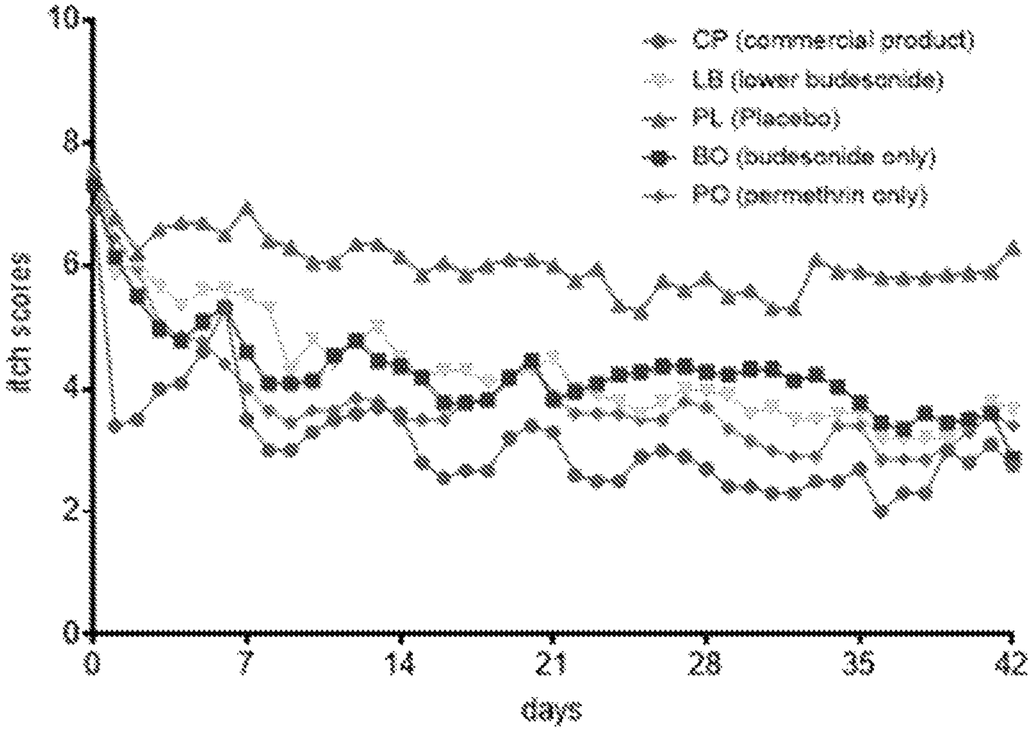
FIG. 2 is a graphical representation showing the itch score for each of the treatment groups in the clinical study of a formulation of permethrin and budesonide for the topical treatment of horses suffering *Culicoides* allergy. The itch score was measured daily for 42 days using the Pruritus Visual Analogue Scale.

Itch score: Itch score was measured daily by the owner in the scale of 0-10 for 42 days using the Pruritus Visual Analogue Scale whereby an itch score from 1-10 is assigned based on various indicators of itch in the horse. At day 0, there was no difference between the treatment groups ($p=0.3360$). At day 42, only the CP was statistically significantly different from placebo ($p=0.0483$). Results are shown in FIG. 2.

Figure 3:
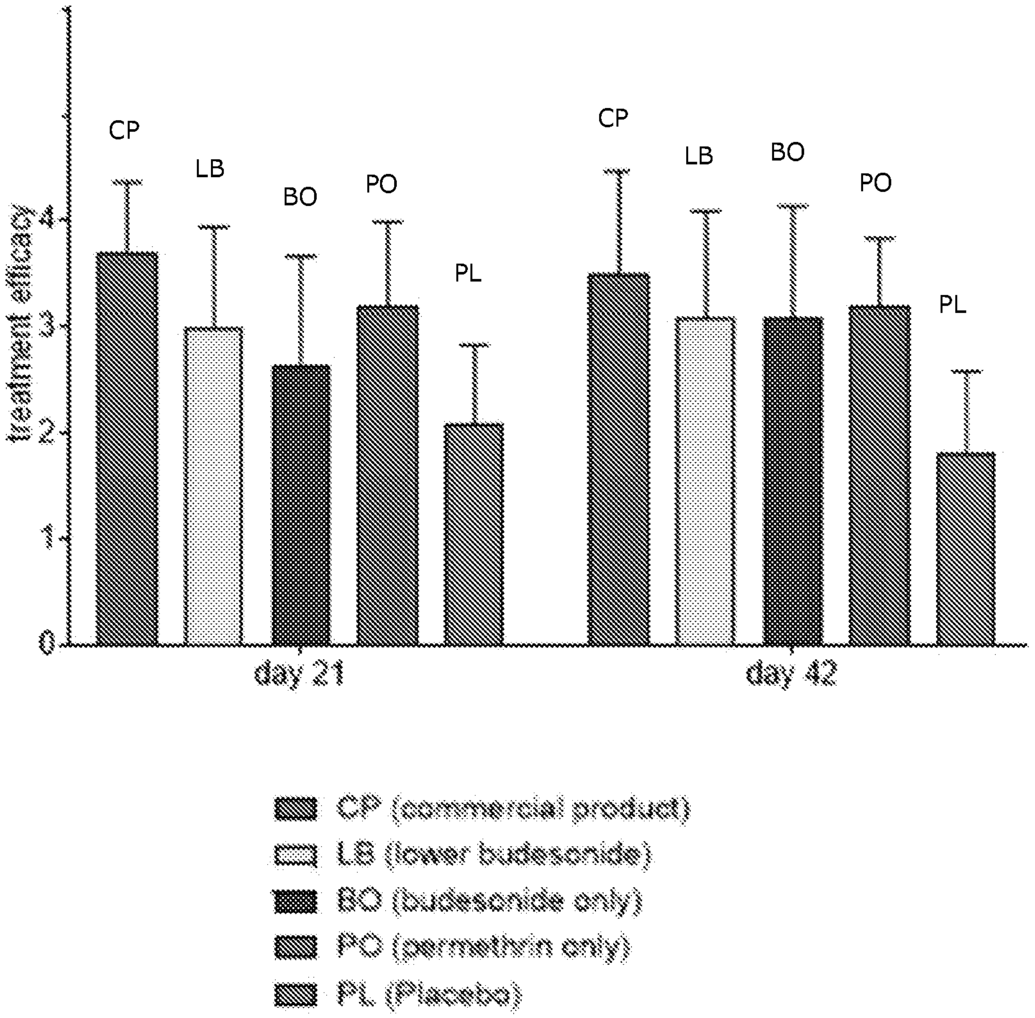
FIG. 3 is a graphical representation summarizing the overall response to treatment in each of the treatment groups of the clinical study. A 4-tiered scale from 1 (poor) to 4 (excellent) is used as an overall improvement measurement and was evaluated by a veterinarian at days 21 and 42.

Overall response to treatment: Overall treatment efficacy scores were on a 4-tiered scale from 1 (poor) to 4 (excellent) and it was used as an overall improvement measurement that was evaluated by veterinarian at days 21 and 42. A total 70% of horses in CP group showed excellent response to treatment at day 21 and 42. At day 21 and 42 only the CP showed statistically significant difference ($p=0.0019$) from the placebo control. (FIG. 3).

Summary: The following table (Table 1) shows the results of all main outcome measures, namely lesion score, itch score, quality of life and overall response of treatment (treatment efficacy).

TABLE 1

| Treatment Group | Lesion Score Day 0 | Lesion Score Day 42 | Itch Score Day 0 | Itch Score Day 42 | Quality of Life Score Day 0 | Quality of Life Score Day 42 | Treatment Efficacy Day 0 | Treatment Efficacy Day 42 |
|---|---|---|---|---|---|---|---|---|
| CP (Example 1) | 74 | 11 | 6.9 | 2.7 | 4.5 | 8.4 | 3.7 | 3.5 |
| LB (Lower budesonide) | 70 | 22 | 7.3 | 3.7 | 4.6 | 7.2 | 3.0 | 3.1 |
| BO (Budesonide only) | 77 | 29 | 7.3 | 2.9 | 4.1 | 8.5 | 2.6 | 3.1 |
| PO (Permethrin only) | 68 | 18 | 7.5 | 3.4 | 4 | 7.7 | 3.2 | 3.2 |
| Placebo/Control (Excipients only) | 74 | 54 | 7.6 | 6.3 | 4.7 | 6.1 | 2.1 | 1.8 |

These data show that CP is the only treatment that shows statistically significant difference in outcome measures of the study compared to placebo. These data demonstrate clear reduction in lesion scores, itch scores and overall response to treatment and increase in quality of life with the formulation of Example 1 (CP).

Sleep data was collected using activity trackers on horses to track their movements. Sleep data was calculated from the time (in minutes) that the horses remained still without any movements. It was observed that horses in the CP treatment group generally spent more time resting than those horses in the other treatment groups. The horses in the Placebo/control treatment group spent the least amount of time resting. These data support the hypothesis that horses treated with the CP composition are less restless and sleep or rest more.

After the initial study, 42 horse owners opted to continue to phase 2 of the trial where they used the product for one year when needed. The results showed most owners used much less than full dose and only used it occasionally. No significant side effects were noted under these conditions.

An animal safety study was performed on healthy horses using 1×, 3× and 5× recommended doses for 6 weeks and 1× dose for 12 weeks. No abnormalities were detected in bloods or skin (biopsies) with 6 weeks full dose or even 5× full dose. The product was thus considered safe to use.

These data demonstrate that the formulations of the invention can be used to treat the symptoms of IBH or Queensland Itch. The symptoms of at least one of the symptoms, comprising excoriations, scale and crust, alopecia and papules, are observed to be reduced quickly and the overall treatment efficacy is considered beneficial. A significant reduction in itching and distress for the horse was generally noted. The affected animal's welfare was observed to be improved with no, or only very minor side effects. This is considered to be useful as an effective safe treatment that works in a reasonable time frame. It requires only weekly application and is devoid of the common complications of systemic corticosteroids. Thus, the formulations of the invention are considered to find use in treatment of an animal suffering from a particularly cruel, painful and distressing disease of IBH.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method of treating insect bite allergic dermatitis in a mammal, the method comprising topical application of a pharmaceutical composition comprising budesonide; permethrin; a silicone excipient; and a pharmaceutically acceptable carrier to the mammal in need thereof.

2. The method according to claim 1, wherein the silicone excipient is selected from one or more of cyclopentasiloxane, cyclotetrasiloxane and dimethiconol.

3. The method according to claim 1, wherein the budesonide is in an amount of about 0.05 g/L to about 1 g/L.

4. The method according to claim 1, wherein the budesonide is in an amount of about 0.25 g/L.

5. The method according to claim 1, wherein the permethrin is in an amount of about 10 g/L to about 60 g/L.

6. The method according to claim 1, wherein the permethrin is in an amount of about 40 g/L.

7. The method according to claim 1, wherein the ratio of budesonide to permethrin is approximately 1:160.

8. The method according to claim 1, wherein the silicone excipient is in an amount of about 25 g/L to about 150 g/L.

9. The method according to claim 1, wherein the silicone excipient is in an amount of about 75 g/L.

10. The method according to claim 1, wherein the composition is a conditioner, a leave-in conditioner, a lotion, a spray, a cream, an ointment or a pour-on formulation.

11. The method according to claim 1, wherein the composition is a leave-in conditioner.

12. The method according to claim 1, wherein the composition is applied by pouring or spraying.

13. The method according to claim 1, wherein the mammal is selected from cattle, pigs, sheep, dogs and equines.

14. The method according to claim 1, wherein the mammal is a dog or equine.

15. The method according to claim 1, wherein the mammal is a horse.

16. The method according to claim 1, wherein the composition is applied to the coat or skin of the backline, mane area, tail area, dorsal midline, ears, head or ventral area of an equine.

17. The method according to claim 1, wherein the composition is applied to the rump, dorsal thorax, flanks, ears, head or perineal area of a dog.

18. The method according to claim 1, wherein the composition comprises:

budesonide in an amount of about 0.05 g/L to about 1 g/L;
permethrin in an amount of about 10 g/L to about 60 g/L;
one or more silicone excipients in an amount of about 25 g/L to about 150 g/L; and
a pharmaceutically acceptable aqueous carrier; and optionally
one or more excipients selected from thickening agents, solubilizing agents, chelating agents, antioxidants, preservatives, and pH modifiers.

19. The method according to claim 1, wherein the composition comprises:

budesonide in an amount of about 0.25 g/L;
permethrin in an amount of about 40 g/L;
one or more silicone excipients in an amount of about 75 g/L;
thickening agents in an amount of about 30 g/L;
one or more excipients selected from solubilizing agents, chelating agents, antioxidants, preservatives, and pH modifiers; and
purified water to 1 L.

20. The method according to claim 19, wherein the thickening agent is a mixture of Polyquaternium-37, propylene glycol dicaprylate/dicaprate and PPG-1 Trideceth-6.

* * * * *